United States Patent [19]

Sigler

[11] 4,081,906
[45] Apr. 4, 1978

[54] CAST CUTTER

[75] Inventor: Thelma G. Sigler, Orange, Calif.

[73] Assignee: Alpha Nova Development Corporation, Santa Ana, Calif.

[21] Appl. No.: 791,865

[22] Filed: Apr. 28, 1977

[51] Int. Cl.² ............................................. B26B 7/00
[52] U.S. Cl. ...................................... 30/276; 30/390
[58] Field of Search .................................. 30/276, 390

[56] References Cited

U.S. PATENT DOCUMENTS

| 1,127,764 | 2/1915 | Huck | 30/294 UX |
| 1,942,766 | 1/1934 | O'Banion | 30/276 X |
| 2,084,488 | 6/1937 | Heller | 30/276 X |
| 2,139,272 | 12/1938 | Jaworski | 30/276 X |
| 2,617,186 | 11/1952 | Pickles | 30/276 X |
| 3,616,488 | 11/1971 | Barefield | 30/276 X |

Primary Examiner—James L. Jones, Jr.
Assistant Examiner—J. T. Zatarga
Attorney, Agent, or Firm—William C. Babcock

[57] ABSTRACT

A hand held electrically driven cutter assembly for removing casts from the body of a patient includes a vertically articulatable bottom plate insertable between the cast and the body surface which on the interior of the cutter assembly forms a switch in series with a trigger switch connected to the main power. Two circular cutters, inclined relative each other, are disposed above and ahead of the bottom plate to open up a kerf therefor. The power to the cutters is transmitted through a pulley and gear combination to be driven by an electric motor. It is this electric motor that is series connected to the bottom plate switch and power will be applied to the cutters only upon upward urging of the cutter assembly.

8 Claims, 5 Drawing Figures

CAST CUTTER

BACKGROUND OF THE INVENTION

1. Field of the Invention

The present invention relates to electrically driven cutters and more particularly to cutters adapted for opening casts on the body of the patient.

2. Description of the Prior Art

Removal of casts from the body of an injured person is a task requiring care and attention to detail in order to avoid additional injury. Most often such tasks have been performed in the past by power driven devices wherein one or more rotary cutters open up the cast for removal. In order to prevent injury, such prior art cutters usually included a bottom plate or shield which is insertable on the interior of the cast, shielding the body surface of the patient from the sharp cutters. Said bottom or shield plates were often suspended from the cutter carriage and as the cut was made the size of the kerf dictated the support structure therefor. The size of the kerf, furthermore, dictates the manipulative convenience of the cutter itself and therefore is both structurally and manipulatively significant in the use intended. In each instance, however, the separation between the cutter edge and the bottom plate has been kept to a minimum and because of the kerf size and the disposition of said plate certain amount of flexure in a support thereof was unavoidable. Thus most prior art cutters of this type would experience certain amount of bottoming out with the resulting production of metal chips and dulling of the cutting edge.

SUMMARY OF THE INVENTION

Accordingly it is the general purpose and object of the present invention to provide a cast cutter which both opens a wide kerf to permit large support structures for the bottom plate, and which furthermore is operative only in an upward bias against the case.

Further objects of the invention are to provide a cast cutter which is conveniently manipulatable and which provides access to various cast contours.

Yet additional objects of the invention are to provide a cast cutter assembly which is convenient in use and provides minimal exposure to the patient.

Briefly these and other objects are accomplished within the present invention by providing a cylindrical housing having a handle disposed on the dorsal side thereof, said handle including a trigger switch for controlling the electrical power input to an electrical motor disposed within the housing. The electrical motor, in turn, through a set of reduction gears drives an upper pulley engaging a drive belt which extends through a cutter support housing to drive two inclined rotary cutters at the bottom end thereof. The alignment of the two cutters is maintained in both a toe in and positive caster orientation to provide a wide kerf at the rear edges thereof for the passage of the bottom plate support. The bottom plate itself is spring mounted for vertical articulation within the cutter support housing, forming on the interior end thereof a normally closed switch which upon an inward articulation of the plate is opened. This normally closed switch is in series with the trigger switch assembly in the handle and therefore will interrupt power to the motor on inward progression of the plate. By virtue of this switch arrangement, bottoming out of the cutters against the bottom plate will concurrently interrupt power to the motor thus reducing the effect of metal to metal contact. Furthermore, by virtue of this arrangement a safe upward bias is required on the bottom plate thus assuring minimal possibilities of contact with the body of the patient.

Within the housing, the motor pinion directly engages a plurality of reduction or change gears which, in turn, terminate in a miter gear arrangement to redirect the rotational axis for the proper alignment with the pulleys. The pulley system, in turn, at the bottom end drives a set of beveled conical gears which, in turn, engage splines extending from the saw blades. By virtue of this arrangement, the necessary toe-in and caster angles may be accommodated for the desired kerf width.

DESCRIPTION OF THE SPECIFIC EMBODIMENT

Figure 1:
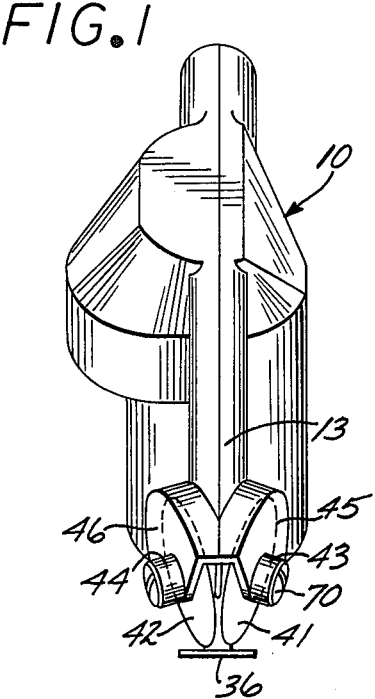
FIG. 1 is a front view of a cutter assembly constructed according to the present invention.
Figure 2:
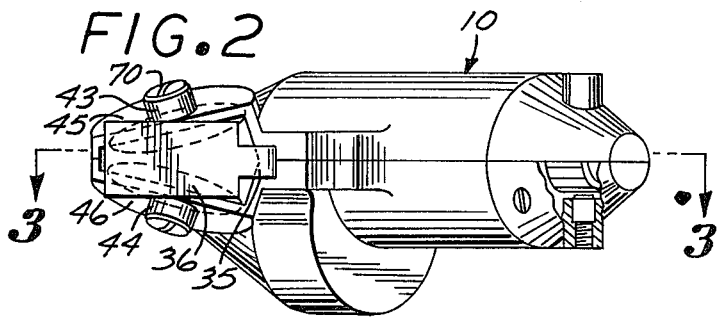
FIG. 2 is a bottom view of the cast cutter assembly shown in FIG. 1.
Figure 3:
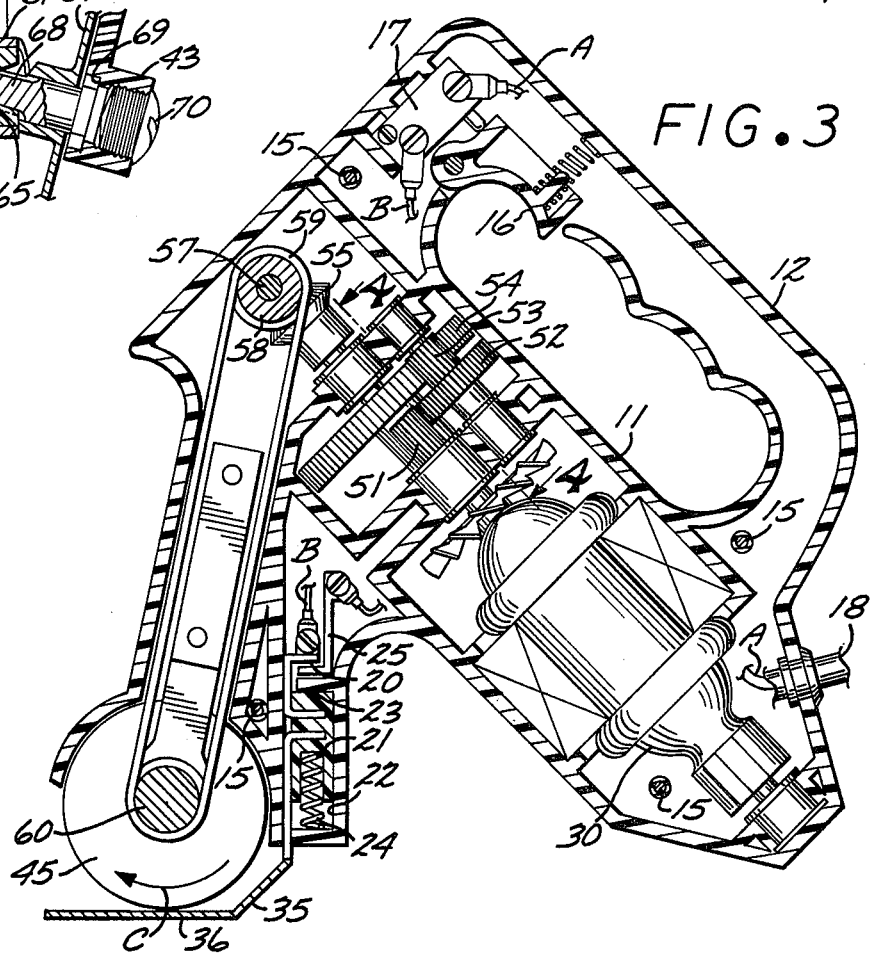
FIG. 3 is a sectional view taken along line 3—3 of FIG. 2.

By reference to FIGS. 1, 2 and 3 the cast cutter assembly, generally designated by the numeral 10, comprises a cylindrical motor housing 11 including a handle 12 on the dorsal side thereof and a cutter support enclosure 13 on the ventral side. Housing 11, handle 12 and cutter enclosure 13 comprise integral parts of a single casting of a material like ABS or similar plastic, cast in two halves and joined in a mating configuration by a plurality of connecting screws 15. Disposed within the handle 12 and extending to the exterior thereof is a pivotally mounted trigger 16 which when articulated depresses a normally open switch 17 connected between an input cord 18, the connection being shown by the letter A for purposes of clarity. The other terminal of switch 17, by way once more of a connection labeled B, connects to a moving terminal 20 disposed within the interior of the cutter support enclosure 13. Terminal 20, in turn, is secured to a plastic slide 21 disposed within a substantially vertical cavity 22 on the interior of the enclosure 13 and biased upwardly against the stop 23 by a spring 24. Thus the articulation of slide 22 concurrently articulates the terminal 20. Another, fixed terminal 25 is in turn disposed for contact with terminal 20 at the downward limit thereof, terminal 25, in turn, completing the circuit to the motor 30 within housing 11.

Attached to slide 21 and extending downwardly to the exterior of the enclosure 13 is a bottom plate assembly 35 terminating in a substantially horizontal bottom plate 36. Plate 36 is aligned below the lower end of enclosure 13 in a position subjacent to the cutting edges of two circular cutters 41 and 42 mounted for rotation within the bottom end of the enclosure.

By reference once more to FIGS. 1, 2 and 3 the alignment of cutters 41 and 42 is both at the toe in and positive caster with the result that the rear edges or the trailing edge of each cutter is separated by a wider gap than the forward or leading edge. This alignment is achieved by virtue of the alignment of two bearing mounts 43 and 44 respectively formed in the lateral surfaces of two semicircular and opposed cutter shields extending from the lower end of enclosure 13.

By virtue of this alignment, and particularly by virtue of the rotational direction shown by arrow C the divergent edges of the cutter are passing downwardly through the cast. This rotational arrangement by virtue of the contact with the cut in the cast tends to urge the cutter assembly 10 upwardly out of the cast, providing the necessary bias against plate 36 to maintain contacts 25 and 20 closed. In case of an inadvertent manual error opposing this direction or in case of fragmentation of the cast edges, any downward motion of the cutter towards plate 36 will concurrently result in an interruption of power to motor 30. Thus the angular arrangement of the cutters and the direction of rotation thereof combines with the action of terminal 20 to provide a safe cooperative arrangement which limits the exposure to potential injury of the patient serviced by the present cutter.

Figure 4:
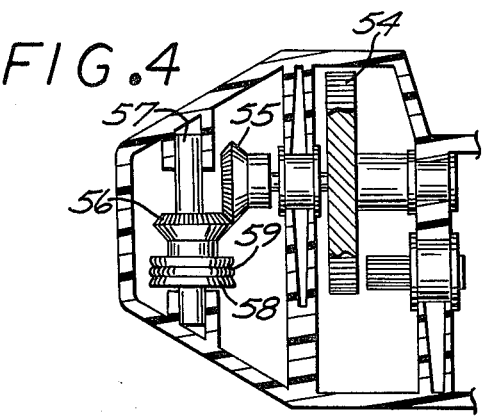
FIG. 4 is yet another sectional view taken along line 4—4 of FIG. 3.
Figure 5:
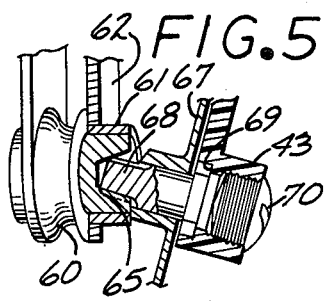
FIG. 5 is a detailed illustration, in partial section, of the structure accommodating the caster and toe-in provisions in the present invention.

By reference to FIGS. 3, 4 and 5, the mechanical power transmission from the motor 30 to the cutters themselves will now be taken up. More specifically, motor 30 terminates on the interior of housing 11 in a pinion 51 engaging a reducing gear 52 secured to get another gear 53 for common rotation. Gear 53, in turn, drives a further reducing gear 54 commonly mounted for concurrent rotation with a miter end gear 55 engage a further miter gear 56. Gear 56, in turn, is engaged to a shaft 57 supporting a pulley 58 engaging the upper end of a drive belt 59. Drive belt 59 extends on the interior of enclosure 13 to engage yet another pulley 60 mounted for rotation in a bearing mount 61 on the lower end of a support leg 62 within the same enclosure. It is the disposition of this support leg 62 and the bearing mounts 43 and 44 formed in the aforementioned cutter shield that provide the necessary engagement for the two cutter blades. More specifically, pulley 60 includes a first and second conical gears 65 and 66 respectively within the lateral end thereof for engagement with the cutting blades. As shown in FIG. 5 conical gear 65 engages a mating spline 68 forming the center axis of blade 41 and terminating at the other side of the same blade in a bearing 69 received within the bearing support 43. A threaded end stop 70 is received within the same bearing support to oppose the spline 68 in its outward progression, thus driving the spline into positive engagement with the conical gear 65.

It is to be noted that while only one side of the cutter assembly is described in FIG. 5, the other cutter is similarly installed. Accordingly while only one support arm 62 is specifically referred to above other structural elements are necessary in order to assure proper axial alignment of the pulley within the enclosure.

The foregoing description of the cast cutter has been set forth with concurrent reference to its operative features. The operation of the present device is therefore concurrently presented above.

Obviously many modifications and variations to the above disclosure can be made without departing from the spirit of the invention. It is therefore intended that the scope of the invention be determined solely dependent on the claims hereto.

I claim:

1. A portable cutter assembly adapted for use in removing casts from the body of a patient, comprising:
   an electrically driven motor adapted for connection to an electric power source;
   gearing coupled to the output of said motor;
   a first housing conformed to receive said motor and said gearing;
   a second housing extending from said first housing and communicating on the interior therewith;
   a first and a second rotary cutter mounted for rotation in said second housing, said first and second rotary cutters having cutting edges partially exposed therefrom, said first and second cutters being aligned at a toe in and positive caster relative each other symmetrically about a longitudinal plane intersecting said first and second housing;
   pulley means disposed on the interior of said first and second housing for transferring rotary power between said gearing and said first and second rotary cutter;
   a bottom plate assembly telescopically received within said second housing and extending outwardly therefrom to align distally subjacent of said exposed edges of said first and second cutters said bottom plate assembly being adapted for telescopic translation relative said cutters;
   spring means disposed in said second housing for urging said bottom plate assembly upwardly towards said cutters;
   a manually operative switch connected in circuit with said motor; and
   a normally open switch connected in series with said manually operative switch, said normally open switch being articulated to a closed state by the downward articulation of said bottom plate assembly.

2. Apparatus according to claim 1 wherein:
   said gearing and pulley means are arranged to advance said cutting edges of said first and second cutters away from said bottom plate assembly and towards the toe in thereof.

3. Apparatus according to claim 2 wherein:
   said first and second housing each comprise a hollow structure separable in mating halves about said longitudinal plane.

4. Apparatus according to claim 3 wherein:
   said bottom plate assembly includes a vertical leg telescopically received in said second housing, said vertical leg being of a transverse dimension smaller than the maximum separation of the cutting edges on said first and second rotary cutter.

5. Apparatus according to claim 4 wherein:
   said first housing is of a substantially cylindrical section; and
   said second housing extends from one end of said first housing, said second housing including an elongate cavity aligned at an acute angle relative said first housing.

6. Apparatus according to claim 5 wherein:
   said first housing includes a handle disposed in said longitudinal plane in distal relationship to said second housing.

7. Apparatus according to claim 6 wherein:
   said normally open includes a contact disposed for articulation by said vertical leg of said bottom plate assembly.

8. Apparatus according to claim 7 wherein:
   said first and second housing comprise plastic castings.

* * * * *